US008648062B2

(12) United States Patent
Haapasalo

(10) Patent No.: US 8,648,062 B2
(45) Date of Patent: Feb. 11, 2014

(54) COMPOSITION AND METHOD FOR IRRIGATION OF A PREPARED DENTAL ROOT CANAL

(75) Inventor: Markus Haapasalo, Vancouver (CA)

(73) Assignee: The University of British Columbia, Vancouver (CA)

( * ) Notice: Subject to any disclaimer, the term of this patent is extended or adjusted under 35 U.S.C. 154(b) by 113 days.

(21) Appl. No.: 12/868,457

(22) Filed: Aug. 25, 2010

(65) Prior Publication Data

US 2011/0054036 A1 Mar. 3, 2011

Related U.S. Application Data

(63) Continuation of application No. PCT/CA2009/000218, filed on Feb. 25, 2009.

(60) Provisional application No. 61/031,254, filed on Feb. 25, 2008.

(51) Int. Cl.
*A61K 31/155* (2006.01)
*A61P 31/04* (2006.01)

(52) U.S. Cl.
USPC .................................................. 514/183

(58) Field of Classification Search
USPC .................................................. 514/183
See application file for complete search history.

(56) References Cited

U.S. PATENT DOCUMENTS 6,365,131 B1 * 4/2002 Doshi et al. ..................... 424/49
6,844,306 B2 * 1/2005 Werle et al. .................... 510/391

FOREIGN PATENT DOCUMENTS

GB 2 453 858 A 4/2009

OTHER PUBLICATIONS

International Preliminary Report on Patentability mailed Sep. 10, 2010, issued in corresponding International Application No. PCT/CA2009/000218, filed Feb. 25, 2009, 9 pages.

González-López, S., et al., "Effect of CHX on the Decalcifying Effect of 10% Citric Acid, 20% Citric Acid, or 17% EDTA," Journal of Endodontics 32(8):781-784, Aug. 2006.

Rasimick, B.J., et al., "Interaction Between Chlorhexidine Digluconate and EDTA," Journal of Endodontics 34(12):1521-1523, Dec. 2008.

Sayin, T.C., et al., "The Effect of EDTA, EGTA, EDTAC, and Tetracycline-HCI With and Without Subsequent NaOCl Treatment on the Microhardness of Root Canal Dentin," Oral Surgery, Oral Medicine, Oral Pathology, Oral Radiology and Endodontics 104(3):418-424, Sep. 2007.

Extended European Search Report and Opinion mailed Mar. 4, 2011, issued in corresponding European Patent Application No. EP 09 71 6002, filed Feb. 25, 2009, 8 pages.

International Search Report mailed Jun. 12, 2009, issued in corresponding International Application No. PCT/CA2009/000218, filed Feb. 25, 2009, 2 pages.

Menezes, A.C.S.C. de, et al., "Smear Layer Removal Capacity of Disinfectant Solutions Used With and Without EDTA for the Irrigation of Canals: a SEM Study," Pesquisa Odontológica Brasileira 17(4):349-355, Oct./Dec. 2003.

Öncağ, Ö, et al., "Comparison of Antibacterial and Toxic Effects of Various Root Canal Irrigants," International Endodontic Journal 36(6):423-432, Jun. 2003.

Portenier, I., et al., "Killing of *Enterococcus faecalis* by MTAD and Chlorhexidine Digluconate With or Without Cetrimide in the Presence or Absence of Dentine Powder or BSA," Journal of Endodontics 32(2):138-141, Feb. 2006.

Vasconcelos, B.C. de, et al., "Cleaning Ability of Chlorhexidine Gel and Sodium Hypochlorite Associated or Not With EDTA as Root Canal Irrigants: A Scanning Electron Microscopy Study," Journal of Applied Oral Science 15(5):387-391, Sep./Oct. 2007.

* cited by examiner

*Primary Examiner* — San-Ming Hui
*Assistant Examiner* — Kathrien Cruz
(74) *Attorney, Agent, or Firm* — Christensen O'Connor Johnson Kindness PLLC

(57) ABSTRACT

Composition and method for irrigating a prepared dental root canal. The composition is an aqueous composition of ethylenediamine tetraacetic acid, chlorhexidine or orally acceptable addition salt, and N-cetyl-N,N,N-trimethylammonium bromide, and is effective for simultaneous smear layer removal and disinfection.

6 Claims, 5 Drawing Sheets

COMPOSITION AND METHOD FOR IRRIGATION OF A PREPARED DENTAL ROOT CANAL

CROSS-REFERENCES TO RELATED APPLICATIONS

This application is a continuation of International Application No. PCT/CA2009/000218, filed Feb. 25, 2009, which claims the benefit of U.S. Provisional Application No. 61/031,254, filed Feb. 25, 2008. Each application is incorporated herein by reference in its entirety.

FIELD OF THE INVENTION

The present invention provides a composition and method for irrigating prepared tooth surfaces. The composition and method remove buildup of undesirable debris formed during the preparation of tooth surfaces during dental procedures and further disinfect the tooth surface. The irrigation composition is an aqueous composition that includes ethylenediamine tetraacetic acid (EDTA), chlorhexidine, and cetrimide.

BACKGROUND OF THE INVENTION

While various chemical and physical irritants can cause irritation and even necrosis of the pulp, the most common causes for pulpal inflammation (pulpitis) are bacteria and/or their products entering the pulp through a deep caries lesion or a leaking filling; an inflammatory reaction in the pulp starts long before bacteria invade the pulp tissue. The inflammatory reaction is first initiated by bacterial antigens interacting with the local immune system. As long as the carious lesion has not entered the pulp, the pulpal inflammation is likely to be reversible. However, when the carious lesion does reach the pulp and the hard tissue barrier is breached, bacteria can invade the pulp. Even after this point, the infection may remain relatively superficial and most of the pulp tissue is vital and bacteria free. For this reason, endodontic treatment of pulpitis should be considered to be treatment of an inflammation and prevention of an infection.

In apical periodontitis, bacteria invade further and colonize the entire root canal system. Apical periodontitis is an inflammatory process in the periradicular tissues caused by microorganisms in the necrotic root canal. Accordingly, to promote healing of apical periodontitis, microorganisms within the root canal system must be eliminated.

Apical periodontitis (AP) is caused by microbes, usually bacteria, residing in the necrotic root canal system of the affected tooth. Although healing of the periapical lesion in some rare cases might be prevented by nonmicrobial factors, microbes are always the etiologic factor in apical periodontitis. The microbes present in the necrotic root canal originate from the oral cavity. However, ecology in the root canal environment is the main factor in the selection of the composition of the infective microflora. As a result of the ecologic pressure, primary apical periodontitis (no previous endodontic treatment) is dominated by anaerobic bacteria, with only a few or no facultative or aerobic species per canal. Endodontic treatment, even when unsuccessful, dramatically changes the ecology in the root canal; availability of oxygen and nutrients is different, and in many cases substances with antimicrobial activity are introduced into the root canal, which might further contribute toward a more resistant, facultative microflora. Post-treatment endodontic infections are therefore dominated by ecologically tolerant bacteria and sometimes also by yeasts, which are characterized by higher resistance to treatment procedures and disinfecting agents than the anaerobic microflora in cases of primary apical periodontitis.

On the basis of our knowledge of the etiology of apical periodontitis, there is a strong consensus that elimination of the microbes in the root canal system is the main immediate goal of the treatment to obtain complete healing of the lesion. There is mounting evidence, however, that obtaining sterility of the infected root canal by presently available treatment methods might be more difficult than once thought.

Locally used endodontic disinfectants, either irrigating solutions or interappointment medicaments, are effective against a wide spectrum of microorganisms. They affect a range of vital functions of the microbial cell, resulting rapidly in cell death. Hypochloric acid interferes with oxidative phosphorylation and other membrane-associated functions of the cell as well as DNA synthesis inside the cell. Hypochlorite is effective against bacteria and yeast; even bacterial spores are killed with high concentration (5%) sodium hypochlorite.

Chlorhexidine (CHX) penetrates the outer cell wall layers of the microbes and attacks the inner membrane, cytoplasmic membrane in bacteria and plasma membrane in yeast cells. In high concentrations CHX has the ability to coagulate intracellular constituents of the microbial cells. The antiviral effect of CHX has also been reported.

The exact mechanism of action of iodine compounds is not fully understood, but these compounds also penetrate into the microorganisms and interact with key molecules of the cells (proteins, fatty acids, and nucleotides). Iodine compounds kill their target cells rapidly, and they are active against bacteria (including spores), fungi, and viruses.

Calcium hydroxide has a high pH, which is the main reason for its antibacterial activity. It has been suggested that the hydroxyl ions denature proteins of the cytoplasmic membrane of bacteria, thus killing the cell. It has been shown with *Enterococcus hirae* that the tolerance to alkaline pH was dependent on a proton antiport system; mutant cells lacking the proton transport system showed highly increased sensitivity to alkali. This was later also confirmed with a strain of *E. faecalis*. The susceptibility to high pH of enterococci and oral yeasts has been compared and found that yeasts were equally or more resistant to high pH by calcium hydroxide than *E. faecalis*. It is likely that tolerance of high pH by oral yeasts is also dependent on a proton pump in the plasma membrane of the yeast cells. Nevertheless, in a saturated calcium hydroxide solution (pH≥12.5) in vitro enterococci were killed within 20 minutes and yeasts within 6 hours.

A mixture of tetracycline isomer (doxycycline), acid, and detergent (MTAD) is a new member in the group of antibacterial root canal irrigants. MTAD contains bacteriostatic antibiotic (doxycycline) in high concentration, which might alter its antibacterial effect to bactericidal, although this has not been directly shown. Other components of MTAD include citric acid and TWEEN 80, which together with doxycycline might have a synergistic effect on the bacterial cell wall and the cytoplasmic membrane.

Despite the advances in the development of root canal irrigation compositions noted above, there exists a need for effective and easy to use compositions for root canal irrigation. The present invention fulfills this need and provides further related advantages.

SUMMARY OF THE INVENTION

The present invention provides a composition and method for irrigating a prepared dental root canal. The composition is a stable aqueous solution of ethylenediamine tetraacetic acid, chlorhexidine or orally acceptable addition salt, and N-cetyl- N,N,N-trimethylammonium bromide, and is effective for simultaneous smear layer removal and disinfection.

In one aspect of the invention, an irrigation composition is provided. In one embodiment, the composition includes ethylenediamine tetraacetic acid, chlorhexidine or orally acceptable addition salt, N-cetyl-N,N,N-trimethylammonium bromide, and water.

In one embodiment, ethylenediamine tetraacetic acid is present in an amount from about 0.5 to about 20 percent by weight of the composition.

In one embodiment, chlorhexidine or orally acceptable addition salt is present in an amount from about 0.01 to about 5.0 percent by weight of the composition.

In one embodiment, N-cetyl-N,N,N-trimethylammonium bromide is present in an amount from about 0.001 to about 3.0 percent by weight of the composition.

In one embodiment, the composition includes ethylenediamine tetraacetic acid in an amount from about 1 to about 17 percent by weight of the composition, chlorhexidine or orally acceptable addition salt in an amount from about 0.1 to about 0.5 percent by weight of the composition, and N-cetyl-N,N,N-trimethylammonium bromide in an amount from about 0.1 to about 0.5 percent by weight of the composition.

In another aspect, the invention provides a method for making a chlorhexidine-containing composition. In one embodiment, the method includes combining chlorhexidine or orally acceptable addition salt and N-cetyl-N,N,N-trimethylammonium bromide in water to provide chlorhexidine-containing aqueous solution; and adding ethylenediamine tetraacetic acid to the chlorhexidine-containing aqueous solution to provide a chlorhexidine-containing composition.

In a further aspect, the invention provides a method for removing smear layer and disinfecting in a root canal. In one embodiment, the method includes irrigating the root canal with a composition that includes ethylenediamine tetraacetic acid, chlorhexidine or orally acceptable addition salt, N-cetyl-N,N,N-trimethylammonium bromide; and water.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
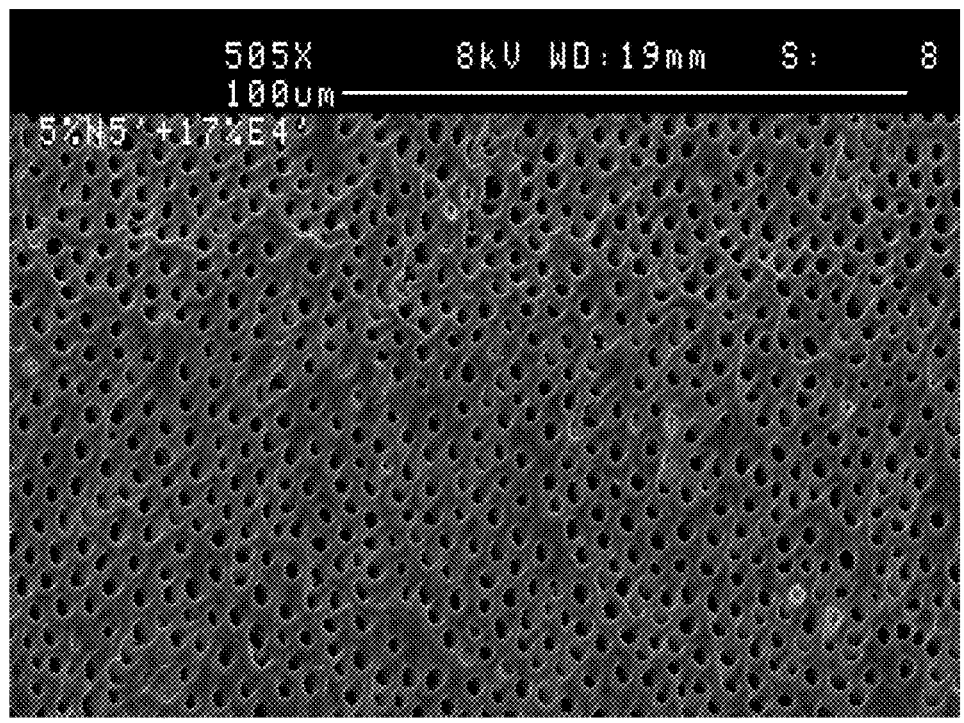
FIG. 1 is a scanning electron microscope image of a tooth surface (control) in which a smear layer was removed by treatment with 5 percent aqueous sodium hypochlorite (5% NaOCl) for 5 minutes followed by treatment with 17 percent aqueous ethylenediamine tetraacetic acid (17% EDTA, disodium, pH 7) for 4 minutes, open dentinal canals are clearly observable.

In one aspect, the invention provides a composition useful for irrigating prepared tooth surfaces. The action of the composition is two-fold. The composition effectively removes buildup of undesirable debris (smear layer) formed during the preparation of tooth surfaces during dental procedures. The composition further disinfects the tooth surface.

The term "smear layer" is known to those of skill in the art of dentistry and refers to the complex accumulation of organic and inorganic debris resulting from the mechanical preparation of a tooth surface. The smear layer includes cutting debris, tooth particles, microorganisms, necrotic material, and other substances resulting form preparation, and can include a superficial layer on the surface of a prepared tooth along with a layer or layers that are packed into the adjacent dentinal tubules at varying depths.

The composition of the invention useful for irrigating prepared tooth surfaces is an aqueous composition that includes ethylenediamine tetraacetic acid (EDTA), chlorhexidine or orally acceptable addition salt, and N-cetyl-N,N,N-trimethylammonium bromide (cetrimide).

Smear layer removal is achieved by the composition, at least in part, by the presence of EDTA. As used herein the term "ethylenediamine tetraacetic acid" or "EDTA" refers to orally acceptable ethylenediamine tetraacetic acid salts including, for example, ethylenediamine tetraacetic acid disodium. Ethylenediamine tetraacetic acid is present in an amount from about 0.5 to about 20 percent by weight of the composition. In one embodiment, ethylenediamine tetraacetic acid is present in an amount from about 1 to about 17 percent by weight of the composition.

As noted above, in addition effectively removing smear layer, the composition further disinfects the tooth surface. Disinfection is due at least in part to the presence of chlorhexidine or orally acceptable addition salt in the composition. As used herein, the term "chlorhexidine" refers to 1,1'-hexamethylenebis[5-(p-chlorophenyl)biguanide], a substance having a strongly basic action with only low water solubility. By reacting chlorhexidine base with acids, water-soluble salts can be obtained. As used herein, the term "chlorhexidine" refers to chlorhexidine in free base form and the term "orally acceptable addition salt" refers to chlorhexidine salts that are acceptable for use as oral irrigating compositions. Suitable orally acceptable chlorhexidine addition salts include chlorhexidine digluconate, chlorhexidine diformate, chlorhexidine diacetate, chlorhexidine dipropionate, chlorhexidine dilactate, chlorhexidine dinitrate, chlorhexidine sulfate, and chlorhexidine tartarate. Chlorhexidine or orally acceptable addition salt is present in an amount from about 0.01 to about 5 percent by weight of the composition. In one embodiment, chlorhexidine or orally acceptable addition salt is present in an amount less than 1.0 percent by weight of the composition. In one embodiment, chlorhexidine or orally acceptable addition salt is present in an amount from about 0.1 to about 0.5 percent by weight of the composition.

The irrigating composition further includes N-cetyl-N,N,N-trimethylammonium bromide (cetrimide), a microbially active quaternary ammonium bromide. N-cetyl-N,N,N-trimethylammonium bromide is present in an amount from about 0.001 to about 3 percent by weight of the composition. In one embodiment, N-cetyl-N,N,N-trimethylammonium bromide is present in an amount from about 0.1 to about 0.5 percent by weight of the composition.

In one embodiment of the composition, ethylenediamine tetraacetic acid is present in an amount from about 1 to about 17 percent by weight of the composition, chlorhexidine or orally acceptable addition salt is present in an amount from about 0.1 to about 0.5 percent by weight of the composition, and N-cetyl-N,N,N-trimethylammonium bromide is present in an amount from about 0.1 to about 0.5 percent by weight of the composition.

The present invention solves the problem associated combining a smear layer remover with a disinfectant. The present composition overcomes the problem of maintaining effective amounts of EDTA and disinfectant (chlorhexidine or orally acceptable addition salt) in solution. Previously, EDTA and chlorhexidine or orally acceptable addition salt could not be prepared having an EDTA concentration sufficient for effective smear layer removal. The present invention solves this problem and provides a ready-to-use irrigation composition that simultaneously effectively removes smear layer and disinfects. The composition of the invention has an EDTA concentration of at least 0.5 percent by weight, up to about 20 percent by weight, and a chlorhexidine or orally acceptable addition salt concentration of at least about 0.1 percent by weight, up to about 5.0 percent by weight. The present invention provides a stable chlorhexidine solution containing up to about 20 percent by weight EDTA.

The composition of the invention offers advantages over a commercially available product, BIOPURE MTAD Cleanser (Dentsply International, York, Pa.), an antibacterial root canal cleanser (smear layer removal and root canal disinfectant). The disinfectant in MTAD is an antibiotic, doxycycline, and does not kill *Enterococcus faecalis* nearly as rapidly as the composition of the present invention. Furthermore, unlike the ready-to-use composition of the invention, MTAD must be prepared chair side by mixing two components either during or immediately before treatment.

In another aspect, a method for making the irrigation composition is provided. In the method, the chlorhexidine-containing composition of the invention is made by combining chlorhexidine or orally acceptable addition salt and N-cetyl-N,N,N-trimethylammonium bromide in water to provide chlorhexidine-containing aqueous solution; and then adding ethylenediamine tetraacetic acid to the chlorhexidine-containing aqueous solution to provide a chlorhexidine-containing composition.

Smear layer removal from instrumented root canal surfaces is essential for effective cleaning and disinfection. Traditionally, EDTA has been used for smear layer removal. However, as noted above, chlorhexidine cannot be combined with high concentration EDTA without precipitation formation and the consequence that the mixture cannot remove the smear layer.

In the method for making the composition of the invention, chlorhexidine is first mixed with cetrimide before EDTA is added. In the method, no precipitate is formed. Without being bound to any theory, chlorhexidine and cetrimide in water appear to form a micelle formulation that protects the combination from precipitation.

In one embodiment of the method, the ratio of N-cetyl-N,N,N-trimethylammonium bromide to chlorhexidine or orally acceptable addition salt is from about 5 to about 1. In one embodiment, the ratio of N-cetyl-N,N,N-trimethylammonium bromide to chlorhexidine or orally acceptable addition salt is from about 3 to about 1. In another embodiment, the ratio of N-cetyl-N,N,N-trimethylammonium bromide to chlorhexidine or orally acceptable addition salt is from about 1 to about 1.

In one embodiment, the chlorhexidine-containing aqueous solution has a chlorhexidine concentration of from about 1 to about 20% by weight.

In one embodiment, the ethylenediamine tetraacetic acid is added as a solid. In another embodiment, the ethylenediamine tetraacetic acid is added as a solution. In this embodiment, the ethylenediamine tetraacetic acid is added as a solution having an ethylenediamine tetraacetic acid concentration of from about 5 to about 50% by weight.

The chlorhexidine-containing composition prepared by the method is an aqueous solution that includes ethylenediamine tetraacetic acid in an amount from about 1 to about 20 percent by weight, chlorhexidine or orally acceptable addition salt in an amount from about 0.01 to about 5.0 percent by weight, and N-cetyl-N,N,N-trimethylammonium bromide in an amount from about 0.001 to about 3.0 percent by weight.

Figure 2:
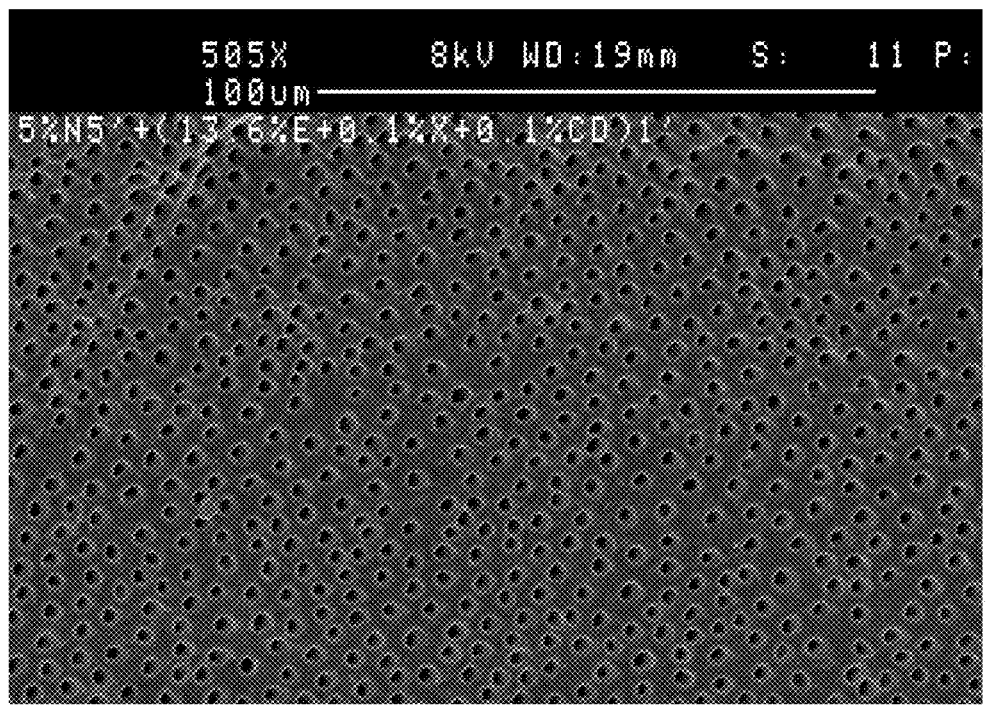
FIG. 2 is a scanning electron microscope image of a tooth surface treated with a representative composition of the invention (Qmix 1); smear layer was removed by treatment with 5% NaOCl for 5 minutes followed by treatment with a representative composition of the invention (13.6 percent by weight EDTA, 0.1 percent by weight chlorhexidine, and 0.1 percent by weight cetrimide in distilled water) for 1 minute, open dentinal canals are clearly observable.
Figure 3:
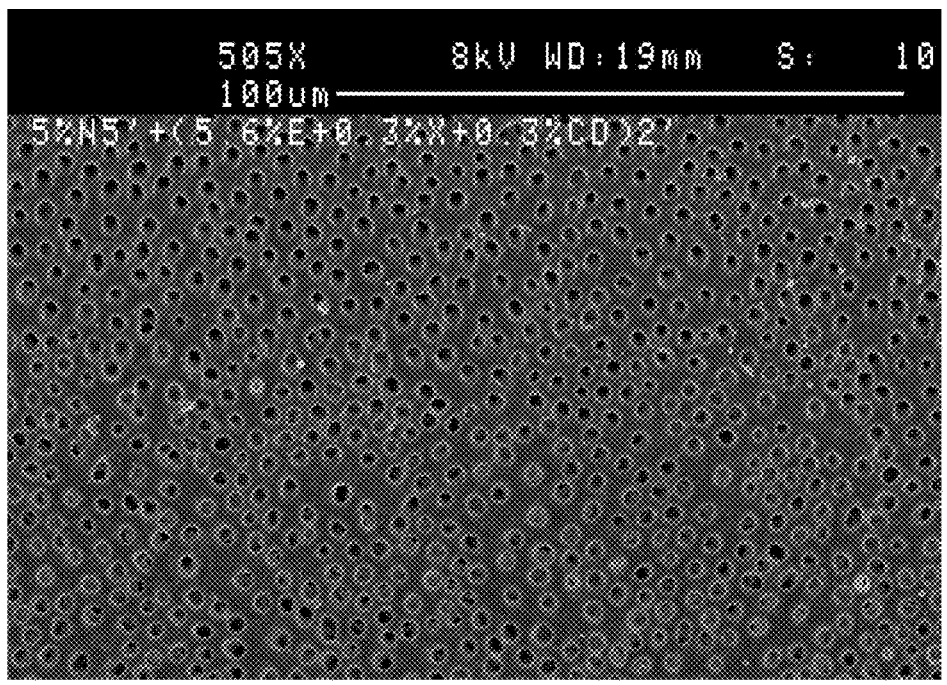
FIG. 3 is a scanning electron microscope image of a tooth surface treated with a representative composition of the invention (Qmix 2); smear layer was removed by treatment with 5% NaOCl for 5 minutes followed by treatment with a representative composition of the invention (5.6 percent by weight EDTA, 0.1 percent by weight chlorhexidine, and 0.1 percent by weight cetrimide in distilled water) for 2 minutes, open dentinal canals are clearly observable.
Figure 4:
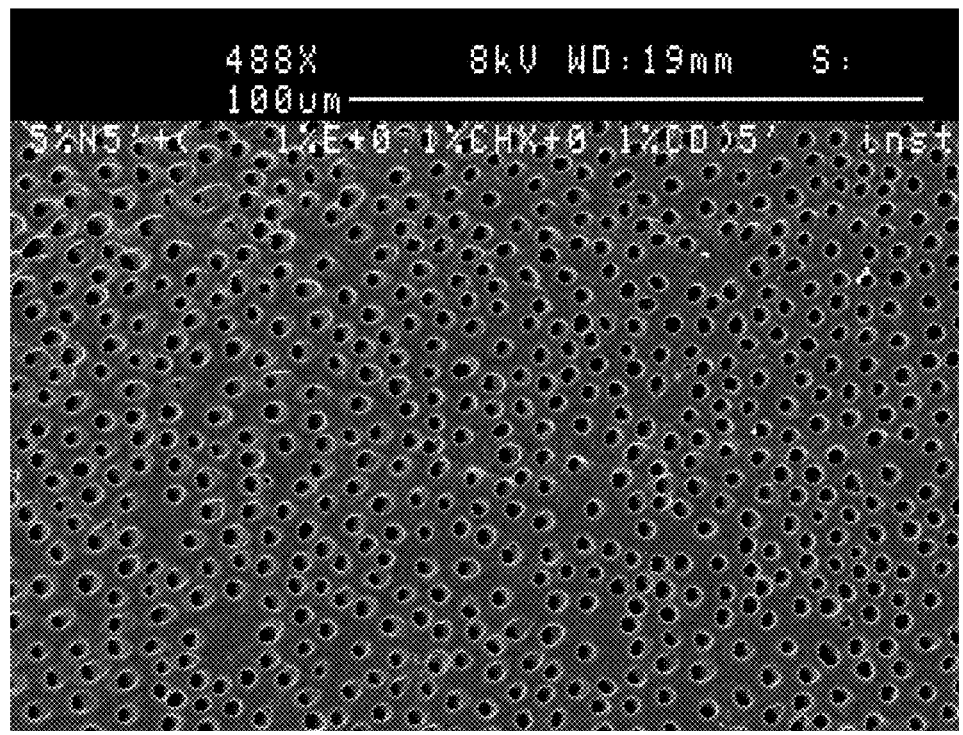
FIG. 4 is a scanning electron microscope image of a tooth surface treated with a representative composition of the invention (Qmix 3); smear layer was removed by treatment with 5% NaOCl for 5 minutes followed by treatment with a representative composition of the invention (1.0 percent by weight EDTA, 0.1 percent by weight chlorhexidine, and 0.1 percent by weight cetrimide in distilled water) for 5 minutes, open dentinal canals are clearly observable.
Figure 5:
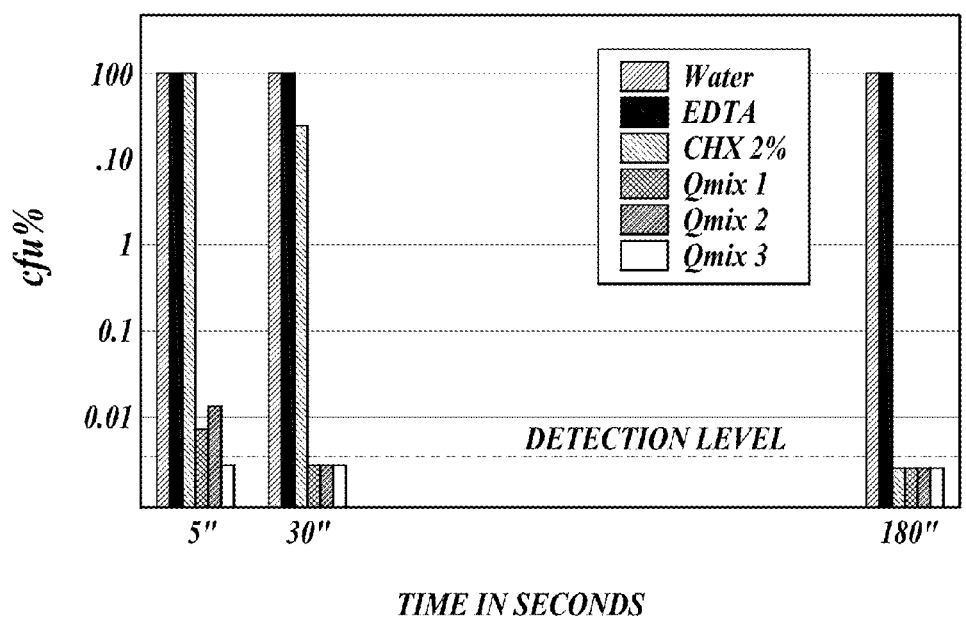
FIG. 5 is a graph comparing the survival of *Enterococcus faecalis* A197A (colony forming units percent, cfu %) after exposure to water, 17% EDTA, chlorhexidine (2 percent by weight in water, CHX 2%, and three representative compositions of the invention (Qmix 1, Qmix 2, and Qmix 3); exposure times were 5 seconds, 30 seconds, and 3 minutes; detection level is at 99.995% killing; survival in water and EDTA was 100% for all exposure times.

The preparation of representative compositions of the invention containing chlorhexidine, cetrimide, and EDTA (13.6, 5.6, and 1.0 percent by weight), are described in Examples 1-3. The efficacy of these compositions in smear layer removal are illustrated in FIGS. 2-4 (17% EDTA control illustrated in FIG. 1). The antibacterial activity of the representative compositions is illustrated in FIG. 5.

The present invention provides a method for removing a smear layer from and sterilizing endodontic excavations and other prepared tooth surfaces by irrigating with a chlorhexidine-containing composition of the invention. Thus, in a further aspect of the invention, a method for irrigating a prepared tooth surface is provided. In the method, a prepared tooth surface is irrigated with a sterile composition comprising ethylenediamine tetraacetic acid, chlorhexidine or orally acceptable addition salt, N-cetyl-N,N,N-trimethylammonium bromide, and water. In one embodiment, the prepared surface is irrigated with sodium hypochlorite prior to irrigating with the composition comprising ethylenediamine tetraacetic acid, chlorhexidine or orally acceptable addition salt, N-cetyl-N,N,N-trimethylammonium bromide, and water.

In one embodiment, the prepared surface is irrigated with a composition that includes ethylenediamine tetraacetic acid in an amount from about 1 to about 17 percent by weight, chlorhexidine or orally acceptable addition salt in an amount from about 0.1 to about 0.5 percent by weight, and N-cetyl-N,N,N-trimethylammonium bromide in an amount from about 0.1 to about 0.5 percent by weight.

The method for irrigating is effective for a variety of prepared tooth surfaces. The surface can be a surface that is an endodontic situs, a surface that is an instrumented root canal, a surface prepared for a periodontic procedure, a surface that is prepared site for tooth restoration, or a surface prepared for tooth reconstruction.

In the method, the surface is irrigated from about 1 minute to about 1 hour. In one embodiment, the surface is irrigated from about 1 minute to about 10 minutes.

The following examples are provided for illustrating, not limiting the invention.

EXAMPLES

Example 1

The Preparation and Effectiveness of a Representative Irrigation Composition: 13.6% EDTA In this example, the preparation and effectiveness of a representative irrigation composition of the invention is described. The composition includes 13.6 percent by weight EDTA, 0.1 percent by weight chlorhexidine, and 0.1 percent by weight cetrimide in distilled water.

A three (3) percent cetrimide solution (by weight) is prepared by mixing cetrimide powder with distilled water. Heating helps dissolution of the powder. Chlorhexidine (CHX) is purchased as a 20% aqueous stock solution. CHX is diluted in distilled water to a 1% solution. A 17% EDTA solution is prepared, the pH is adjusted to 7 by adding sodium hydroxide (thus EDTA becomes disodium EDTA). To make 100 ml of the irrigation solution, the ingredients are mixed as follows: 10 ml of 1% CHX solution is added to 10 ml of 3% cetrimide solution. After gentle mixing, 80 ml of 17% EDTA solution is added, and the solution is gently mixed. This solution contains EDTA (13.6%), cetrimide (0.3%) and chlorhexidine (0.1%).

The effectiveness of the composition in removing smear layer was evaluated by treating a smear layer in a root canal with 5% NaOCl for 5 minutes followed by treatment with the representative composition prepared as described above for 1 minute. The effectiveness of the composition in removing the smear layer is illustrated in FIG. 2 where open dentinal canals are clearly observable.

The antibacterial activity of the composition was evaluated by exposing a planktonic culture (in suspension) of *Enterococcus faecalis* A197A, a resistant bacterial species often isolated from treatment resistant endodontic infections (root canal infections). In the evaluation, cultures were exposed for 5 seconds, 30 seconds, and 3 minutes. Detection level was at 99.995% killing.

Survival of *E. faecalis* in water and EDTA was 100% for all exposure times. The representative composition killed *E. faecalis* in seconds, and was superior to 2% chlorhexidine alone. The effectiveness of the composition in killing *Enterococcus faecalis* A197A is illustrated in FIG. 5.

Example 2

The Preparation and Effectiveness of a Representative Irrigation Composition: 5.6% EDTA In this example, the preparation and effectiveness of a representative irrigation composition of the invention is described. The composition includes 5.6 percent by weight EDTA, 0.1 percent by weight chlorhexidine, and 0.1 percent by weight cetrimide in distilled water.

This representative composition was prepared as described above, except that the EDTA solution was a 5.6 percent by weight EDTA solution.

The effectiveness of the composition in removing smear layer was evaluated by treating a smear layer in a root canal with 5% NaOCl for 5 minutes followed by treatment with this representative composition for 2 minutes. The effectiveness of the composition in removing the smear layer is illustrated in FIG. 3 where open dentinal canals are clearly observable.

The antibacterial activity of the composition was evaluated as described above in Example 1. The representative composition killed *E. faecalis* in seconds, and was superior to 2% chlorhexidine alone. The effectiveness of the composition in killing *Enterococcus faecalis* A197A is illustrated in FIG. 5.

Example 3

The Preparation and Effectiveness of a Representative Irrigation Composition: 1.0% EDTA In this example, the preparation and effectiveness of a representative irrigation composition of the invention is described. The composition includes 1.0 percent by weight EDTA, 0.1 percent by weight chlorhexidine, and 0.1 percent by weight cetrimide in distilled water.

This representative composition was prepared as described above, except that the EDTA solution was a 1.0 percent by weight EDTA solution.

The effectiveness of the composition in removing smear layer was evaluated by treating a smear layer in a root canal with 5% NaOCl for 5 minutes followed by treatment with this representative composition for 5 minutes. The effectiveness of the composition in removing the smear layer is illustrated in FIG. 4 where open dentinal canals are clearly observable.

The antibacterial activity of the composition was evaluated as described above in Example 1. The representative composition killed *E. faecalis* in seconds, and was superior to 2% chlorhexidine alone. The effectiveness of the composition in killing *Enterococcus faecalis* A197A is illustrated in FIG. 5.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composition, comprising:
   (a) ethylenediamine tetraacetic acid;
   (b) chlorhexidine or orally acceptable addition salt;
   (c) N-cetyl-N,N,N-trimethylammonium bromide; and
   (d) water, wherein the composition is in the form of an aqueous solution.

2. The composition of claim 1, wherein ethylenediamine tetraacetic acid is present in an amount from about 0.5 to about 20 percent by weight of the composition.

3. The composition of claim 1, wherein the orally acceptable addition salt is chlorhexidine digluconate.

4. The composition of claim 1, wherein chlorhexidine or orally acceptable addition salt is present in an amount from about 0.01 to about 5.0 percent by weight of the composition.

5. The composition of claim 1, wherein N-cetyl-N,N,N-trimethylammonium bromide is present in an amount from about 0.001 to about 3.0 percent by weight of the composition.

6. The composition of claim 1, wherein ethylenediamine tetraacetic acid is present in an amount from about 1 to about 17 percent by weight of the composition, chlorhexidine or orally acceptable addition salt is present in an amount from about 0.1 to about 0.5 percent by weight of the composition, and N-cetyl-N,N,N-trimethylammonium bromide is present in an amount from about 0.1 to about 0.5 percent by weight of the composition.

* * * * *